US011518720B2

(12) United States Patent
Stemwedel (10) Patent No.: US 11,518,720 B2
(45) Date of Patent: Dec. 6, 2022

(54) MANUFACTURING PROCESS FOR PRODUCING AMMONIA FROM ANAEROBIC DIGESTATE LIQUID (71) Applicant: CALIFORNIA ORGANIC FERTILIZERS, INC., Hanford, CA (US)

(72) Inventor: Timothy Stemwedel, Hanford, CA (US)

(*) Notice: Subject to any disclaimer, the term of this patent is extended or adjusted under 35 U.S.C. 154(b) by 0 days.

(21) Appl. No.: 16/866,505

(22) Filed: May 4, 2020

(65) Prior Publication Data
US 2020/0346986 A1 Nov. 5, 2020

Related U.S. Application Data (60) Provisional application No. 62/842,103, filed on May 2, 2019.

(51) Int. Cl.
| C05C 3/00 | (2006.01) |
| C05G 5/23 | (2020.01) |
| C05F 11/02 | (2006.01) |
| C12P 3/00 | (2006.01) |
| C05F 17/00 | (2020.01) |
| C02F 11/04 | (2006.01) |
| C02F 11/02 | (2006.01) |
| C02F 11/13 | (2019.01) |

(52) U.S. Cl.
CPC ............ *C05C 3/00* (2013.01); *C02F 11/02* (2013.01); *C02F 11/04* (2013.01); *C02F 11/13* (2019.01); *C05F 11/02* (2013.01); *C05F 17/00* (2013.01); *C05G 5/23* (2020.02); *C12P 3/00* (2013.01)

(58) Field of Classification Search
None
See application file for complete search history.

(56) References Cited

U.S. PATENT DOCUMENTS

| 4,372,856 A | 2/1983 | Morrison |
| 4,710,300 A | 12/1987 | Kristoufek |
| 6,342,378 B1 | 1/2002 | Zhang et al. |
| 6,464,875 B1 | 10/2002 | Woodruff |
| 6,521,129 B1 | 2/2003 | Stamper et al. |
| 6,682,578 B2 | 1/2004 | Sower |
| 7,056,482 B2 | 6/2006 | Hakka et al. |
| 7,416,644 B2 | 8/2008 | Bonde |

(Continued)

FOREIGN PATENT DOCUMENTS

| CN | 103241827 | 8/2013 |
| DE | 102005017077 | 10/2006 |

(Continued)

OTHER PUBLICATIONS

The Facts About Ammonia, Jun. 15, 2021 in U.S. Appl. No. 16/402,188.

(Continued)

*Primary Examiner* — Wayne A Langel
(74) *Attorney, Agent, or Firm* — Sierra IP Law, PC; William K. Nelson (57) ABSTRACT The present invention relates to organic nitrogen fertilizers and methods for producing organic nitrogen fertilizers, including retrieving high concentration organic ammonia from discarded organic material.

19 Claims, 2 Drawing Sheets

(56) References Cited

U.S. PATENT DOCUMENTS

| | | | |
|---|---|---|---|
| 7,892,310 B2 * | 2/2011 | Le | C02F 1/5254 |
| | | | 71/25 |
| 7,947,105 B2 | 5/2011 | Burnham | |
| 8,613,894 B2 * | 12/2013 | Zhao | C12P 3/00 |
| | | | 423/168 |
| 8,992,654 B2 | 3/2015 | Dahms et al. | |
| 9,452,938 B2 | 9/2016 | Orentlicher et al. | |
| 10,106,447 B2 * | 10/2018 | Orentlicher | B01D 61/025 |
| 2001/0037976 A1 | 11/2001 | Blonigen et al. | |
| 2005/0005660 A1 | 1/2005 | Burnham et al. | |
| 2006/0213370 A1 | 9/2006 | Leonard et al. | |
| 2008/0302722 A1 | 12/2008 | Burke | |
| 2009/0206028 A1 | 8/2009 | Jiang et al. | |
| 2010/0139345 A1 | 6/2010 | Burnham | |
| 2010/0201026 A1 | 8/2010 | Dvorak et al. | |
| 2013/0133386 A1 | 5/2013 | Baker et al. | |
| 2013/0283872 A1 * | 10/2013 | Bisson | C05F 3/00 |
| | | | 71/21 |
| 2014/0037570 A1 | 2/2014 | Whitehurst et al. | |
| 2014/0199743 A1 | 7/2014 | Hughes et al. | |
| 2014/0346108 A1 | 11/2014 | Josse et al. | |
| 2014/0363344 A1 * | 12/2014 | Orentlicher | C02F 1/44 |
| | | | 422/148 |
| 2014/0367345 A1 | 12/2014 | Greene et al. | |
| 2016/0355443 A1 | 12/2016 | Burnham et al. | |
| 2017/0166488 A1 | 6/2017 | Chaudhry | |
| 2017/0183272 A1 | 6/2017 | Sanders | |
| 2019/0367382 A1 * | 12/2019 | Rapport | B01D 61/16 |

FOREIGN PATENT DOCUMENTS

| | | |
|---|---|---|
| GB | 2256154 | 8/1994 |
| JP | 2001137888 | 5/2001 |
| WO | 2009059615 | 5/2009 |
| WO | 2016075709 A2 | 5/2016 |
| WO | 2019213461 | 11/2019 |

OTHER PUBLICATIONS

Li et al., English Abstact of CN103241827, Published by Espacenet, available at https://worldwide.espacenet.com/publicationDetails/biblio?CC=CN&NR=103241827A&KC=A&FT=D#.

Spindler et al., English Abstact of DE102005017077, Published by Espacenet, available at https://worldwide.espacenet.com/publicationDetails/biblio?CC=DE&NR=102005017077B4&KC=B4&FT=D#.

Fujise et al., English Abstact of JP2001137888A, Published by Espacenet, available at https://worldwide.espacenet.com/publicationDetails/biblio?CC=JP&NR=2001137888A&KC=A&FT=D#.

International Search Report for PCT/US20/31385 dated Oct. 16, 2020.

* cited by examiner

MANUFACTURING PROCESS FOR PRODUCING AMMONIA FROM ANAEROBIC DIGESTATE LIQUID

FIELD OF THE INVENTION

The present invention relates to methods of extracting ammonia from digestate liquids produced through anaerobic digestion processes. The methods of the present invention yield ammonia compounds generated through biological processes and in high concentration.

DISCUSSION OF THE BACKGROUND

Organic farming is a highly regulated segment of the agricultural industry. Government entities such as the US Department of Agriculture (USDA) and various state agencies have formulated strict rules (e.g., under the Organic Foods Production Act) governing the growing and handling techniques required for products labeled as "organic". These regulations are generally aimed at maintaining ecological and environmental conditions, and providing healthy foods. The demand for organic foods is rapidly increasing due to environmental stewardship concerns, and consumer preference. Thus, many portions of the agricultural industry have become focused on organic alternatives to conventional methods of production, including using organic pesticides, herbicides, and fertilizers. Regulatory, environmental, and health concerns are primary reasons for using natural or organic products.

As such there is a substantial potential market for fertilizers and other products that comply with the regulations for growing, harvesting or otherwise processing and/or obtaining organic food products. However, the existing chemical fertilizers are generally prohibited in organic farming, and composts and manures are commonly used as fertilizers instead. Composts and manures are often insufficient to generate desired crop yield, and thus supplemental nitrogen is often needed in organic cropping systems. The industry has faced difficulties in finding economically efficient and effective organic chemical agents and natural materials, including nitrogen fertilizers that can be used in the industry. Thus, the agricultural industry faces significant challenges in productivity and efficiency in the area of organic farming.

There continues to be a particular need in organic farming for more effective fertilizers to replace compost and other nitrogen sources that provide insufficient nitrogen. Finding economical and efficient alternatives to existing sources of nitrogen for use in organic farming has yielded little success. Therefore, improved and efficient compositions of naturally produced nitrogenous compounds are needed.

SUMMARY OF THE INVENTION

The present invention provides methods of extracting ammonia from digestate liquids produced through anaerobic digestion processes. The extracted ammonia can be then be incorporated into organic fertilizers compositions. The ammonia and other nitrogenous compounds may be recovered from the digestate generated by an anaerobic digestion process, which are conventionally used to process organic waste and produce methane gas. The natural sources of nitrogenous compounds may be organic wastes generated by food processing plants, bio-digesters, rendering plants, dairies, and other sources. The nitrogen compounds may also be derived from rich organic liquid materials, such as wastewater sludge, slurry from slaughter houses, fowl manures, etc.

The ammonia and nitrogen compounds captured using the present invention are extracted from natural sources of nitrogenous compounds, without chemical reactions, and thus provides an organic source of nitrogen compounds (e.g., particularly aqueous ammonia) that can be used in fertilizer compositions for use in organic farming. The resulting organic fertilizers may be liquid or solid organic fertilizers for organic agriculture obtained by extracting nitrogenous compounds from discarded organic materials. The fertilizer composition may include the organically derived nitrogenous compounds at a concentration in a range of about 3% to about 30% by weight.

The inventive method may include a process that utilizes a series of desorption and absorption stages. The removal of ammonia from solution may be accomplished at a pH in a range of about 8 to about 12, to allow the dissociation of ammonium ion into aqueous ammonia and a hydrogen ion. The process may also utilize the effect of temperature on the dissociation of the ammonium ion. Increased temperature results in the dissociation of ammonium at lower pH ranges allowing more ammonia recovery at a lower pH.

Figure 1:
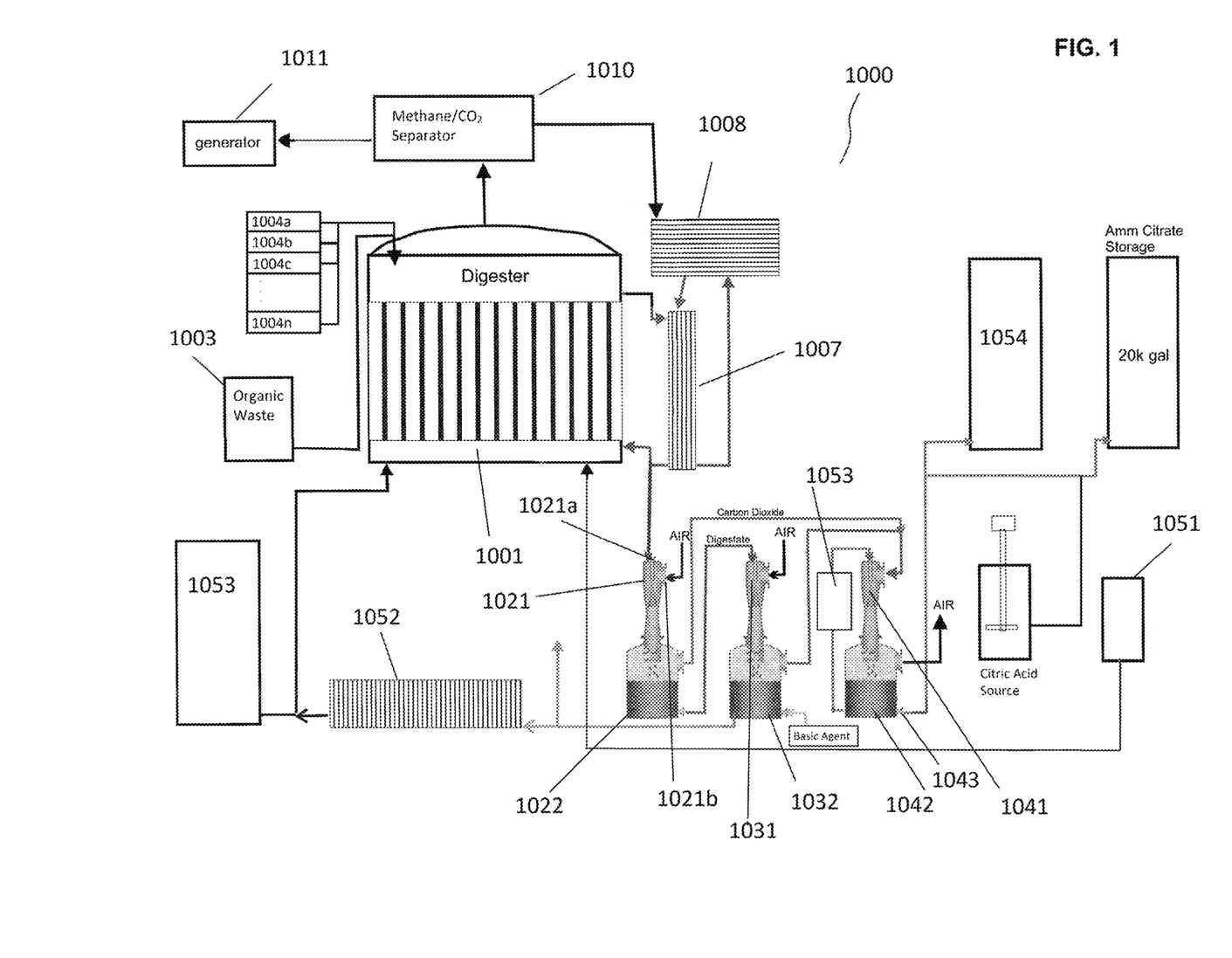
FIG. 1 provides a schematic view of an ammonia capture system, according to an embodiment of the present invention.
Figure 2:
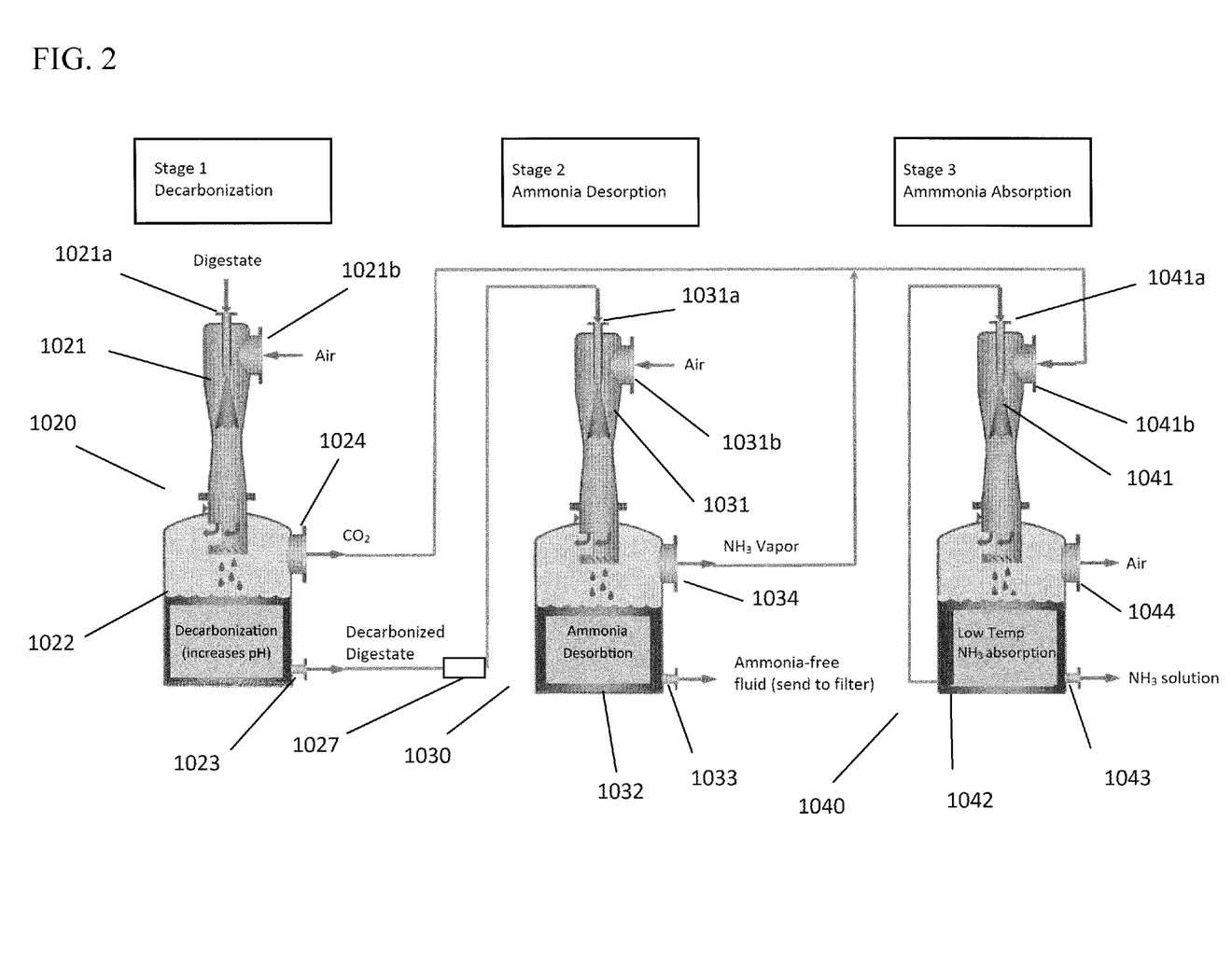
FIG. 2 provides a schematic view of collection apparatus of an ammonia capture system, according to an embodiment of the present invention.

Described below is a method and system for producing an aqueous ammonia product from organic waste materials through physical processes without the need for chemical reactions, thereby yielding an organic nitrogen source that complies with current regulatory agency regulations (e.g., as the FDA and the USDA National Organic Program [NOP]) for use in organic farming. The method and system is described with reference to FIGS. 1 and 2 submitted herewith. FIG. 1 provides a schematic view of an ammonia recovery system. FIG. 2 provides a view of a sequence of injector tubes and collection chambers utilized within the ammonia recovery system in a stepwise process of decarbonization of a digestate, desorption of ammonia from the decarbonized digestate, and ammonia reabsorption in an aqueous solution. The following description should be read with reference to FIGS. 1-2.

The discarded organic material used for the digestion/extraction process may be from various organic substrate sources, including plant biomass, manure, other animal waste, municipal and food wastes, supplemented with additional materials that improve the yield of desired ammoniacal products from the digestion. The discarded organic material may be processed through a non-chemical microbe-mediated digestion process to produce a liquid byproduct rich in ammonia and ammonium compounds. Such organic materials may be utilized in the extraction process disclosed herein. The digestion process may be an anaerobic digestion process that produces ammonia and ammonium compounds as byproducts.

In order to maximize the ammonia and ammonium compound production in the biodigestion process, a co-digestion process may be used in some embodiments. The co-digestion may utilize a balance of substrates, including a major substrate available in large amounts (e.g. manure or sewage sludge) and additional minor co-substrates present in smaller amounts for purposes of balancing the chemistry of co-digestion to facilitate the generation of ammonia and ammonium compounds in the biodigestion process. Co-digestion improves nutrient balance and digestion, equalization of solids by dilution, biogas production, and increases the potential for production of ammonia and ammonium compounds produced by natural means without chemical reactions, while producing higher yields of ammonia and ammonium compounds.

Anaerobic bacteria may be used in the biodigestion process. In biodigestion, high fermentation rates from proteins from animal derived co-substrates result in the formation of ammonia. Thus, biowastes high in proteins (e.g., slaughter house wastes) are ideal for producing a substrate for the ammonia extraction process disclosed herein. However, the production of large concentrations of ammonia in the biodigestion process can raise pH and inhibit other desirable digestion processes, such as contemporaneous methanogenesis. Thus, co-digestion with other substrates, such as manure and nutrient supplements that supply sodium, calcium, magnesium, and trace amounts of nickel, cobalt, molybdenum, and/or selenium can counter-act the effects of increased ammonia and hydrogen sulfide and other inhibitory chemical products of the anaerobic digestion. An alternative biodigestion substrate that is able to produce high levels of ammonia is a combination of manure, plant biomass, general municipal sewage, and other low-protein materials with non-synthetic high-protein supplements such as blood meal, blood, soy meal, soy derived proteins, meat meal (slaughter house waste), feather meal, fish and fish by-products, whey, milk, dairy by-products, alfalfa, corn, and sweet clover. Such proteinaceous co-substrates provide nutrients missing from biodigestion of low-protein materials and help to prevent inhibiting substances from affecting methanogenesis. Additional feedstock may include molasses, sugar beet molasses, sugar reduces molasses, and vinasse, providing high sugar content to promote anaerobic respiration. Betaine may be added as a supplemental organic nitrogen source for bacterial digestion in some implementations.

Exemplary substrates and additives for anaerobic digestion include blood meal, whey, alfalfa, corn, sweet clover, and/or molasses, which can be mixed with the discarded organic material (such as manure or municipal waste). Blood meal is a high protein, low fat animal product that provides high levels of nitrogen for ammonia production. The low fat content reduces the amount of fatty acids and other byproducts that create inefficiencies in the biodigestion process. Sweet clover is a nutrient rich and widely available legume that contains 15% protein. Alfalfa is also highly digestible, readily providing the nutrients therein for the anaerobes in the biodigestion mixture. Thus, blood meal and/or sweet clover (and other high nitrogen organic matter, such as sweet clover and corn) are exemplary additives that can be loaded into the digesters along with the organic waste materials to create a high-nitrogen effluent. The nitrogen in the effluent may be predominantly in the form of ammonia and ammonium, with other ammoniacal compounds.

The conditions in the digestor may be maintained in ranges that are conducive to anaerobic respiration and the production of ammonia by methanogenic and other anaerobic bacteria present in the biodigestor, such as *Streptococcus, Enterobacterium*, and *Methanolobus* strains. The pH and temperature may be held in pre-determined ranges. In some embodiments, the pH of the biodigestor may be in a range of about 30° C. and about 360° C. (e.g., between about about 40° C. and about 50° C.). The temperature of the digestor may be maintained by a combination of the heat generated by the anaerobic metabolism of the anaerobic bacteria in the digestor and one or more heating mechanisms for heating feedstock for the digestor and/or the digestate fluid in the digestor. For example, the system may include a boiler that provides steam for a heat exchanger through which digestate fluid is passed to increase the temperature thereof and then the digestate fluid may be returned to the digestor. In some examples, the boiler may be fueled by methane gas that is generated in the digestor and then extracted by a methane/$CO_2$ separation system, further discussed below.

The pH of the biodigestor may be maintained in a pH range of about 6.5 to about 9 (e.g., in a range of about 6.8 to about 7.5, or any value therein). In some embodiments, bacterial strains that are able to thrive and produce ammonia at higher pH levels may be selected for use in the biodigestor (e.g., *Methanolobus* strains such as *Methanolobus bombayensis, Methanolobus taylorii*, and *Methanohalophilus zhilinaeae*). In such embodiments, the pH of the biodigestor may be maintained at a higher pH in a range of about 7 to about 9.5 (e.g., about pH 7.5 to about pH 8.5, or any pH value therein). In some examples, the pH of the digestor may be maintained at the pre-determined range by the combination of the degassing and removal of $CO_2$ from the digestate liquid and the addition of a basic agent into digestor as needed. For example, the digestor may include one or more pH meters that are in communication with an electronic controller that is operable to control a valve and pump for releasing a basic agent of predetermined concentration and known basicity from a storage container housing the basic agent. The basic agent may be NaOH, $Ca(OH)_2$, KOH, hydrated lime, or other basic agent. Hydrated lime may be used in some implementations, and is approved under some agency regulations for use on "organic" crops.

The ammonia-rich liquid effluent created by the biodigestion process may subsequently be used in the ammonia extraction process of the present invention. The method of extracting ammonia and ammonium species (e.g., ammonia, ammonium, ammonium hydroxide, and ammonium carbonate) from the effluent includes optimizing the chemical condition of the effluent by increasing the temperature and/or pH of the effluent to degas carbon dioxide from the effluent and increase the pH thereof, to drive the chemical equilibrium of ammonium bicarbonate and free ammonia in the effluent toward the release of more free ammonia, and then extracting $NH_3$ and other ammoniacal compounds from the effluent. The recovery of the ammonia and other ammoniacal compounds in the optimized effluent may be accomplished through a sequence of desorption and absorption stages in which the physical conditions of the effluent (e.g., temperature and pH) are varied to facilitate removal and reabsorption of ammonia in aqueous solution.

Digestate liquid from a digestor apparatus (e.g., an anaerobic digestor) may have large amounts of dissolved carbon dioxide and carbonic acid. The removal of carbon dioxide from the digestate fluid is desirable for the purposes of recovering ammonia because it raises the pH of the digestate which drives the equilibrium of ammonium species (e.g., ammonium bicarbonate) towards dissociation. This process of "decarbonization" results from the inverse relationship between carbon dioxide solubility in water and increased solution temperature. Carbon dioxide degasses from the digestate fluid as the temperature of the solution rises pushing the equilibrium of carbonic acid toward dissociation into $CO_2$ and water, thereby reducing the hydrogen ion concentration and the raising the pH of the digestate fluid. The heating of the digestate has the further effect of "deacidifying" the digestate. A significant amount of $CO_2$ may evolve from the digestate in the digestor, due to the sustained warm conditions therein. The pH at which $CO_2$ degasses from the effluent is lower than the pH at which the $NH_3$ degasses from the effluent and forms $NH_3$. As an example, $CO_2$ degasses from the effluent in pH range of about pH 6 to about pH 8 (e.g., about pH 6.5 to about pH 7.5) at a temperature of about 60° C., whereas $NH_3$ degasses from the effluent in pH range of about pH 8 to about pH 11 (e.g., about pH 8.5 to about pH 10) at a temperature of about 60° C. As the $CO_2$ degasses from the effluent, the effluent becomes less acidic because the equilibrium of carbonic acid and $CO_2$ shifts to $CO_2$, which then evaporates removing $CO_2$ and carbonic acid from the system and increasing the pH. Thus, the desorption process proceeds in a stepwise manner, with the $CO_2$ being removed first under lower pH conditions and the ammonia vapor being removed subsequently under higher pH conditions.

Methane may also be produced in the digestor by anaerobic bacteria contained in the mixture. The methane and $CO_2$ gas that evolves in the digestor may be collected via ducting and transferred to a methane/$CO_2$ separation system. For example, a Generon® $CO_2$ separation system or other separation system may be used to separate the methane and $CO_2$ gases evolved from the digestate in the digestor. The separated methane may be utilized as a fuel for a boiler for providing heated water or other fluid used in heat exchangers in the system for heating fluids at various stages of the ammonia recovery process, including heating the digestor and/or the feedstocks added into the digestor. Steam from the boiler may also be routed to mix with the recovered ammonia and vapor at one or more mixing stages to heat the recovered ammonia product. The methane may additionally or alternatively used as a fuel for an electric generator. The recovered $CO_2$ may be vented out of the system and/or routed to mix with a recovered ammonia vapor before the ammonia vapor is introduced into a third mixing stage to lower the pH of the recovered ammonia mixture.

The digestate fluid from the digestor may be collected and heated to drive further carbon dioxide out of solution from the digestate fluid. The temperature of the digestate fluid may be raised to a temperature of about 50° C. to about 100° C., and preferably greater than 60° C. The digestate may be heated in a heat exchanger, in a heating chamber, or by other heating apparatus. The heated digestate fluid may subsequently passed through a Venturi-style injector tube, while air is injected into the heated digestate through an injector duct at the low-pressure choke point of the Venturi injector tube. The air is mixed thoroughly with the digestate in the turbulent flow of the Venturi injector tube, providing a high degree of surface area interface between the digestate fluid and the injected air. This results in an enhanced degassing of $CO_2$ from the digestate. The digestate/air mixture passes from the Venturi injector tube into a chamber in which the digestate/air mixture settles, and the $CO_2$-rich air bubbles out of the digestate fluid. In some examples, the resulting decarbonization of the digestate may result in the digestate having a pH of about 8 to about 10 (e.g., about 8.5 to about 9.5, or any value in such range). The $CO_2$-rich air may be removed from the chamber for use in a later stage of the ammonia recovery process. The removal of the $CO_2$-rich air may be aided by a pump, a partial vacuum, or may be allowed to flow naturally from the chamber. The heating and mixing/injection process may remove up to about 90% of the $CO_2$ from the effluent, thereby pushing the chemical equilibrium of ammonium species (e.g., ammonium bicarbonate and ammonium hydroxide) and ammonia significantly toward free ammonia and increase the pH of the digestate fluid, thereby facilitating an extraction of a greater quantity of ammonia from the effluent.

The decarbonized digestate fluid is left in the chamber. The increased pH of the digestate fluid, in turn, pushes ammonium equilibrium toward dissociation of ammonium into aqueous ammonia and hydrogen ions, making more ammonia available in the digestate fluid and facilitating the recovery of ammonia from the digestate fluid. The decarbonized digestion fluid may then be transported out of the chamber and may be further treating prior to passage through a second stage, an ammonia desorption stage. In some examples, the digestate fluid may be routed to a heat exchanger or other heating apparatus to further raise the temperature of the decarbonized digestate fluid to a temperature in a range of about 70° C. to about 90° C. (e.g., about 75° C. to about 80° C., or any value or range of values therein) prior to passing through a second air nozzle or Venturi tube. The decarbonized digestate at a high temperature and an increased pH allows a large majority of the ammonium in the digestate fluid to become dissociated into ammonia and hydrogen ions, allowing a proportion of the ammonia in solution that is in the uncharged (non-ionized) ammonia state of about 0.6 or greater. The proportion of the ammonia/ammonium equilibrium that is in the $NH_3$ form in an aqueous solution (1) at a temperature in a range of 70° C. to about 80° C. and (2) a pH of about 8 to about 10 (e.g., in a range of about 8.5 to about 9.5) is in a range of about 0.6 to about 0.95. Thus, a large majority of the ammonia in the decarbonized digestate fluid is in recoverable form after it is heated. Additionally, the solubility of $NH_3$ in an aqueous solution is low, and thus most of the $NH_3$ volatilizes from the digestate fluid providing a recoverable $NH_3$ vapor in the second collection chamber.

The heated digestate may be passed through a second air nozzle or Venturi injector tube, while air is injected into the heated digestate through an injector duct at the low-pressure choke point of the Venturi injector tube. A gas (e.g., air, a similar gas mixture, or other gas) is mixed thoroughly with the decarbonized digestate in the turbulent flow of the Venturi injector tube, providing a high degree of surface area interface between the digestate fluid and the injected air. The digestate/air mixture passes from the Venturi injector tube into a chamber in which the digestate/air mixture settles. Due to the high temperature, high pH and high $NH_3$ concentration conditions of the digestate, a substantial amount of ammonia volatilizes, escaping the digestate fluid into the injected air. An ammonia-rich air mixture may be collected from the chamber, through a conduit to a later stage of the ammonia recovery process. The removal of the ammonia-rich vapor may be aided by a pump, applied partial vacuum, or may be allowed to flow naturally from the chamber.

In some embodiments, one or more basic chemical agents may be used to raise the pH of the digestate pooled in the second collection chamber. In some examples, the basic agent may be NaOH, $Ca(OH)_2$, KOH, hydrated lime, or other basic agent, which may be added in sufficient amounts to raise the pH of the pooled digestate to a pH in the range of about 8 to about 11 (e.g., about pH 8.5 to about pH 9.5) to further shift the ammonia equilibrium toward deionized ammonia. The basic agent may be supplied from the storage container for the basic agent discussed above.

In some embodiments, some or all of the fluid remaining in the second collection chamber may be removed from the chamber and routed either back to the digester or delivered into a filtering apparatus for purification. The filtering apparatus may be any of various known filtering apparatus. In some embodiments, the filter apparatus may be a filter press. Once the recovered fluid is filtered, yielding a water filtrate, the water may be conditioned to a target temperature and routed to one or more subsequent uses. The recovered digestate fluid may be conditioned in a heating system (e.g., a heat exchanger electrical heating system, etc.) to a temperature in a range of about 35° C. about 45° C. and routed to a tank for storage. The fluid may be added back to the digester to be mixed with the biodigestion medium as needed. After filtering, the fluid may also or alternatively be conditioned to a temperature of about 75° C. to about 80° C. (e.g., using a heat exchanger or other heating mechanism) and may be added back to the fluid of the second chamber as needed. The filtered fluid may also be conditioned with a pH agent (e.g., sodium hydroxide or lime, etc.) to raise the pH before it is added back to the second tank. Keeping the digestate pooled in the second collection chamber allows for building $NH_3$ concentration in the fluid in the second collection chamber to increase the amount of $NH_3$ that volatilized from the fluid in the second collection chamber.

The $NH_3$ vapor collected from the second collection chamber may be routed to a third Venturi mixer and a third collection chamber. The $NH_3$-rich air may be passed through the injector duct of the third air nozzle or Venturi injector tube and mixed at the throat thereof with the cooled aqueous solution (less than about 20° C.), which has a pH of less than about 8.5. The cooled fluid may be a pH treated solution comprising a weak acid and/or buffering agents to maintain the pH below about 8.5. In some embodiments the cooled fluid passed through the third air nozzle or Venturi mixer may be fluid from the third collection chamber. A portion of the fluid in the third collection chamber may be cooled and recycled and then used as the fluid passed through the air nozzle or Venturi mixer to mix with the $NH_3$-rich air from the second collection chamber. The fluid from the third collection chamber may be collected and routed through a cooling mechanism (e.g., a heat exchanger, refrigeration unit, or other cooling mechanism) and then passed at a pre-determined rate through the third air nozzle or Venturi mixer.

In some embodiments, $CO_2$ gas captured evolved and collected from the digestate fluid in the first mixing chamber may be routed to the injector duct of the third mixing chamber and mixed with the $NH_3$-rich air collected from the second chamber. The added $CO_2$ gas may be used as the means by which the pH of the third collection chamber can be reduced in order to increase the amount of dissolved $NH_4^+$ in the fluid collected in the third mixing chamber. In some embodiments, the $CO_2$ gas may cooled in a heat exchanger or other mechanism prior to it being delivered to the injector duct of the third Venturi mixer.

A substantial amount of the $NH_3$ in the air mixture is able to be dissolved into the cooled, lower pH aqueous solution. The ammonia solubility in aqueous solutions increases as temperature and pH drop. The proportion of ammonia/ammonium equilibrium that is in the $NH_4^+$ form in a aqueous solution (1) at a temperature in a range of 20° C. and (2) a pH of less than about 8.5 is more than about 0.8. Thus, the solubility of $NH_3$ in aqueous solution is also high, and thus a significant proportion of the $NH_3$ in the $NH_3$-rich air dissolves into the ammonia solution. This chemical characteristic is taken advantage of in the presently disclosed invention to recapture the degassed ammonia from the second collection chamber in a filtered aqueous solution that can be practically used in a number of applications including making organic nitrogen fertilizers. The ammonia-rich aqueous solution may be transported incrementally to a holding tank for the clean aqueous ammonia product.

The ammonia solution produced by this process is usable in organic farming. The ammonia is produced at a concentration in a range of about 15-30% w/w of ammonia and ammonium species (e.g., ammonium, ammonium hydroxide, and ammonium carbonate). The organic ammonia solution may be used to create fertilizer compositions that are compliant with the Organic Foods Production Act of 1990, USDA Organic Regulations, (generally referred to as the National Organic Program or NOP) and other agency standards for use in organic farming and can be used in organic farming operations. In some embodiments, the ammonia composition may be mixed with other plant and soil nutrient compounds that are compatible with organic farming to create a nitrogen-rich organic fertilizer composition.

In some embodiments, and without limitation, an ammonia fertilizer composition may include a liquid composition that includes about 3% to about 30% ammonia w/w (e.g., 10% w/w to about 25% w/w, or any value or range of values therein), and/or one or more additional ingredients. The fertilizers may further include organic acids that may serve to balance the pH effects of the concentrated ammonia in the fertilizer. The pH may be maintained in a range around neutral pH, such as between about pH 6 and pH 8 (e.g., from about pH 6.5 to about pH 7.5). To balance the pH of the liquid fertilizer, the liquid fertilizer may include one or more organic acids (e.g., citric acid).

Because the ammonia is organically derived from biowastes and natural sources, the concentration of the stable $^{15}N$ isotope in the resulting ammonia composition is much higher than in ammonia products that are made from chemical syntheses and conventional concentration techniques. The $^{15}N$ isotope is present in the environment and in ammonia products generated by chemical reactions in an amount of about 0.3% per mole of naturally occurring nitrogen. The amount of $^{15}N$ isotope in the ammonia and related species present in recovered nitrogen constituents of the present invention is several times greater than in ammonia products produced by chemical reactions or in natural concentration. The $^{15}N$ isotope in the ammonia and related ammoniacal species present in recovered nitrogen constituents of the present invention is in the range of about 1% to about 20% per mole of nitrogen (e.g., in a range of about 5% to about 15%). The high concentration of $^{15}N$ isotope reflects the process of concentrating ammonia from natural biowastes and nutrient stocks through organic processes.

The resulting high concentration ammonia composition may be further processed into fertilizer products. In some embodiments, the fluid product captured from the third collection chamber may be itself utilized as a fertilizer composition. Such fertilizer composition may be an aqueous solution comprising ammonia and ammonium species in a concentration of about 3% to about 30% w/w (e.g., 10% w/w to about 25% w/w, or any value or range of values therein), and carbonic acid in various soluble forms in an amount of about 5% to about 15% w/w.

In other embodiments, the organic fertilizers may include ammonia and ammonium species in a concentration of about 3% to about 30% w/w (e.g., 10% w/w to about 25% w/w, or any value or range of values therein) and one or more weak organic acids or salts thereof (e.g., polyprotic organic acids or salts thereof), such as citric acid, malic acid, fumaric acid, salts of such organic acids, and combinations thereof. Other simpler organic acids, such as acetic acid salts of such organic acids may be used as well. The organic acids must be from organically-compliant sources (e.g., NOP compliant). Citric acid may be preferred due to its tri-protic chemistry and superior buffering capabilities. The organic acid(s) may be present in a concentration in the liquid fertilizer in a range of about 5% to about 50% w/w, depending on the concentration of ammonia in the liquid fertilizer. For example, the concentration of citric acid in the liquid fertilizer by weight may be about twice the amount of ammonia present in the solution by weight. Simpler monoprotic acids may be present in higher concentrations, due to their lower buffering capacity.

The organic fertilizers of the present invention may also include humic acids which help with nitrogen fixation in the organic fertilizers. Liquid ammonia fertilizers may suffer from nitrogen loss through the evaporation or other pathways of loss. Planting soils are typically acidic to optimize conditions for the growth of plants, which exhibit optimal germination and growth in a pH range of about pH 5.0 to about pH 7.0. The acidic pH of the soil can increase ammonia volatilization. This particularly significant where the fertilizer composition has a relatively high nitrogen concentration (e.g., greater than 10% w/w), since the higher concentration results in a higher rate of volatilization. Humic acids are able to retain $NH_4$ as well as aid in $NH_3$ ammonia volatilization reduction. Humic acids have high cation exchange capacity (CEC) that allows it to retain soil cations and can significantly reduce $NH_3$ volatilization upon addition to an acidic soil (e.g., through the addition of peat). The addition of humic acids to the organic $NH_3$ fertilizer of the present invention significantly reduces $NH_3$ volatilization and lead to effective accumulation of $NH_4$ in the planting soil, despite having an acidic pH (e.g., about pH 5.5 to about 7.0). The humic acids may provide the additional benefit of providing short carbon-chain molecules Humic acids may be included in the organic fertilizer composition of the present invention in a concentration in a range of about 3% w/w to about 8% w/w. The amount of humic acids included in the organic fertilizer may vary with the concentration of ammonia provided therein. For example, in compositions comprising about 10% to about 15% $NH_3$ w/w, the fertilizer composition may include about 3% to about 4% w/w of humic acids. In compositions comprising about 15% to about 25% organic $NH_3$ w/w, the fertilizer composition may include about 5% to about 8% w/w of humic acids.

The organic fertilizer composition of the present invention may also include additional components routinely used in the art, for example, humectants, adjuvants, antioxidants, stabilizers, plant macronutrients, plant micronutrients, and combinations thereof.

The organic fertilizer composition of the present invention may also include a solid fertilizer composition comprising about 3% to about 30% ammonia w/w (e.g., 10% w/w to about 25% w/w, or any value or range of values therein), and/or one or more additional ingredients. The fertilizers may further include organic acids that may serve to balance the pH effects of the concentrated ammonia in the fertilizer. The pH may be maintained in a range around neutral pH, such as between about pH 6 and pH 8 (e.g., from about pH 6.5 to about pH 7.5). The solid fertilizer composition may additionally include humectants, adjuvants, antioxidants, stabilizers, plant macronutrients, plant micronutrients, and combinations thereof. The fertilizer composition may include further nutrients, such as gypsum as a calcium sulfate source, and dolomitic lime as a calcium carbonate and magnesium carbonate source.

It is an objective of the present invention to provide improved organic fertilizers that include an organic nitrogen source that complies with regulatory agencies, such as the FDA and NOP.

It is a further objective of the present invention to provide improved methods for producing concentrated ammonia from a natural source without chemical reactions.

It is a further objective of the present invention to provide improved organic fertilizer compositions having a high concentration of naturally derived ammonia. Existing OIM products are low in the ammonia form of nitrogen. Increased levels of nitrogen will result in a greater availability of ammonia and nitrate nitrogen. The ammonia may then be converted to nitrates by nitrifying bacteria in the soil.

In one aspect, this invention relates a method for manufacturing aqueous ammonia from discarded organic material, comprising the steps of i) collecting nitrogen-rich organic material from a facility, such as a food processing plants, rendering plants, dairies, and other sources; ii) conducting a biodigestion of the discarded organic material in combination with one or more other nutrient feedstock(s); iii) separating the liquid portion (biodigestion effluent) of the biodigested organic material; iv) heating the biodigestion effluent to decarbonize the effluent, v) passing the effluent through a mixing device to inject air into the effluent to remove carbon dioxide, vi) passing the decarbonized effluent through a second mixing device to mix it with air to remove gaseous ammonia from the decarbonized effluent, and vii) injecting the gaseous ammonia into an aqueous solution at a lowered temperature and pH to reabsorb the ammonia in solution, thereby producing an aqueous ammonia product using physical processes, without utilizing chemical reactions.

In a second aspect, this invention relates a method for manufacturing a liquid nitrogen fertilizer from discarded organic material, comprising the steps of i) heating and/or raising the pH of ammonia rich effluent to degas carbon dioxide from the effluent; ii) volatilizing the ammonia from the decarbonized effluent by passing the decarbonized effluent through an air nozzle or Venturi injector tube and mixing the effluent with air to extract ammonia vapor; iii) reabsorbing the ammonia vapor in an aqueous solution; and iv) concentrating the extracted ammonia in a liquid solution, and combining the liquid solution into a liquid fertilizer composition.

In a third aspect, the present invention relates to a method of producing organic ammonia, comprising heating a nitrogen-containing organic substrate in an anaerobic digester device to drive a biological anaerobic digestion of the substrate to yield a digestate; collecting an effluent of the digestate; heating the effluent to evolve $CO_2$-laden gas from the effluent to produce a decarbonized effluent; injecting air into the decarbonized effluent to extract $NH_3$ from the decarbonized effluent in an air/$NH_3$ solution; and cooling the air/$NH_3$ solution to yield an aqueous $NH_3$ product derived from the nitrogen-containing organic substrate without chemical reactions. The step of heating the effluent may drive the chemical equilibrium of ammonium bicarbonate toward the production of $NH_3$ and $CO_2$. The method may further comprise injecting air into the effluent during the step of heating the digestate to produce a decarbonized effluent, wherein injecting air into the digestate includes passing the effluent through a first Venturi injector tube and injecting air into the effluent through the Venturi injection port. The step of injecting air into the decarbonized effluent to extract $NH_3$ from the decarbonized effluent may include passing the decarbonized effluent through a second Venturi injector tube and injecting air into the decarbonized effluent through the Venturi injection port. The method may further comprise injecting the air/$NH_3$ solution into a cooled aqueous $NH_3$ solution to resorb $NH_3$ from the air/$NH_3$ solution during the step of cooling the air/$NH_3$ solution, wherein injecting the air/$NH_3$ solution into a cooled aqueous $NH_3$ solution includes passing the cooled aqueous $NH_3$ solution through a third Venturi injector tube and injecting the air/$NH_3$ solution into the cooled aqueous $NH_3$ solution through the Venturi injection port. The method may further comprise adding a basic chemical agent to the decarbonized effluent before or during the step of extracting $NH_3$ from the decarbonized effluent. The method may further comprise transferring the decarbonized effluent to a filtering apparatus and filtering the decarbonized effluent to yield water, and supplying the water to a collection chamber.

In a fourth aspect, the present invention relates to a liquid organic nitrogenous fertilizer composition, comprising an aqueous solution of the aqueous $NH_3$ product comprising nitrogen that includes molar percentage of $^{15}N$ of about 1% to about 20% of the total molar nitrogen in the aqueous $NH_3$ product. The composition may further comprise an organic acid in a concentration of about 6% to about 50%. The composition may further comprise humic acids as a chelation agent for the ammonia. The humic acids may be present in a concentration of about 3% to about 8%. The concentration of organically produced ammonia may be in a concentration of about 10% w/w to about 20% w/w. The concentration of the organic acid may be in a concentration of about 20% w/w to about 40% w/w. The organic acid may be a triprotic acid. The organic acid may be citric acid. The concentration of organically produced ammonia may be in a concentration of about 10% w/w to about 20% w/w. The concentration of the organic acid may be in a concentration of about 20% w/w to about 40% w/w.

In a fifth aspect, the present invention relates to a liquid organic nitrogenous fertilizer composition, comprising an aqueous solution of aqueous $NH_3$ product produced without chemical reactions and having a concentration of $NH_3$ and other ammoniacal species in a range of about 3% to about 30% by weight. The nitrogen present in the composition may include a molar percentage of $^{15}N$ of about 1% to about 20% of the total molar N in the composition. The composition may further comprise an organic acid in a concentration of about 6% to about 50%. The composition may further comprise humic acids as a chelation agent for the ammonia. The humic acids may be present in a concentration of about 3% to about 8%. The concentration of organically produced ammonia may be in a concentration of about 10% w/w to about 20% w/w. The concentration of the organic acid may be in a concentration of about 20% w/w to about 40% w/w. The organic acid may be a triprotic acid. The organic acid may comprise citric acid.

In a sixth aspect, the present invention relates to a method of producing organic ammonia, comprising heating a nitrogen-containing organic substrate to yield a nitrogen-rich digestate; collecting an effluent of the digestate; heating the effluent to evolve $CO_2$-laden gas from the effluent to lower a pH of the effluent and to produce a decarbonized effluent; passing the decarbonized effluent through a Venturi injector tube and injecting air into the decarbonized effluent to cause degassing of $NH_3$ vapor; and cooling the $NH_3$ vapor to yield an aqueous $NH_3$ solution. The step of heating the effluent may drive the chemical equilibrium of ammonium bicarbonate toward the production of $NH_3$ and $CO_2$. The method may further comprise injecting air into the effluent during the step of heating the effluent to produce the decarbonized effluent, wherein injecting air into the effluent includes passing the effluent through a second Venturi injector tube and injecting air into the effluent through the Venturi injection port. The method may further comprise injecting the $NH_3$ vapor into the aqueous $NH_3$ solution to resorb $NH_3$ from the $NH_3$ vapor, wherein injecting the $NH_3$ vapor into the aqueous $NH_3$ solution includes passing the aqueous $NH_3$ solution through a third Venturi injector tube and injecting the $NH_3$ vapor into the aqueous $NH_3$ solution through the Venturi injection port of the third Venturi injector tube. The method may further comprise adding a basic chemical agent to the decarbonized effluent before or during the step of extracting $NH_3$ from the decarbonized effluent. The method may further comprise transferring the decarbonized effluent to a filtering apparatus and filtering the decarbonized effluent to yield water, and supplying the water to a collection chamber. The method may further comprise injecting $CO_2$ into the aqueous $NH_3$ solution to lower the pH of the aqueous $NH_3$ solution to aid in resorbing $NH_3$ from the $NH_3$ vapor, wherein injecting the $CO_2$ into the aqueous $NH_3$ solution includes passing the aqueous $NH_3$ solution through a third Venturi injector tube and injecting the $CO_2$ into the aqueous $NH_3$ solution through the Venturi injection port of the third Venturi injector tube.

DETAILED DESCRIPTION

Reference will now be made in detail to certain embodiments of the invention, examples of which are illustrated in the accompanying drawings. While the invention will be described in reference to these embodiments, it will be understood that they are not intended to limit the invention. To the contrary, the invention is intended to cover alternatives, modifications, and equivalents that are included within the spirit and scope of the invention. In the following disclosure, specific details are given to provide a thorough understanding of the invention. However, it will be apparent to one skilled in the art that the present invention may be practiced without all of the specific details provided.

Reference will be made to the exemplary illustrations in the accompanying drawings, and like reference characters may be used to designate like or corresponding parts throughout the several views of the drawings.

The present invention concerns systems and methods of extracting ammonia, ammonium, and derivatives thereof from digestate liquids produced through anaerobic digestion processes. The extracted ammonia and related compounds can then be incorporated into organic fertilizer compositions. The ammonia and other nitrogenous compounds may be recovered from the digestate generated by an anaerobic digestion process using a digester and ammonia recovery system, as described herein.

FIG. 1 of the present invention provides a system view of an exemplary system for extracting ammonia and related compounds and derivatives from organic wastes, which may be mixed with various feedstocks. The organic wastes may be processed through a non-chemical microbe-mediated digestion process to produce a liquid byproduct rich in ammonia and ammonium compounds. The system 1000 may include several separation stages to generate and separate ammonia and related compounds and derivatives, and, optionally, other useful byproducts, such as methane.

In some implementations, the organic waste may be added into the digester 1001 from a reservoir 1003 for each digestion process. One or more organic substrate sources, including plant biomass, manure, other animal waste, municipal and food wastes may be stored in and supplied from the reservoir 1003. Other co-substrates for purposes of balancing the chemistry of co-digestion and to facilitate the generation of ammonia and ammonium compounds in the biodigestion process may be fed from separate reservoirs 1004a-1004n. For example, a high protein supplement feedstock may be provided from 1004a, such as for providing non-synthetic high-protein supplements such as blood meal, blood, soy meal, soy derived proteins, meat meal (slaughter house waste), feather meal, fish and fish by-products, whey, milk, dairy by-products, alfalfa, corn, and sweet clover. Fermentation of high levels of proteins from animal derived co-substrates result in increased formation of ammonia. Thus, high protein co-substrates increase the amount of ammonia produced and extracted from the digestate. Other supplements providing sugars and/or other nutrients may be stored in and provided from other reservoirs, such as reservoirs 1004b and 1004c. For example, molasses and/or vinasse may be supplied from reservoir 1004b. Co-digestion utilizing such co-substrates improves nutrient balance and digestion, equalization of solids by dilution, biogas production, and increases the potential for production of ammonia and ammonium compounds produced by natural means without chemical reactions, while producing higher yields of ammonia and ammonium compounds.

The digester 1001 may have a large volume capacity in a range of about 10,000 gallons to about 500,000 gallons, for example, about 50,000 gallons to about 450,000 gallons, about 100,000 gallons to about 400,000 gallons, about 150,000 gallons to about 350,000 gallons, or any value therein. In other examples, the digester may have a smaller volume range for small output to supply relatively small operations or lab research operations. For example, the digester may have a capacity of about 250 gallons to about 10,000 gallons, or any value therein. The digester may be of various types, such as a fixed dome biogas digester, tube digester, or thin film digester.

The environment in the digester 1001 may be conditioned to promote the metabolism and growth of anaerobic (e.g., methanogenic) bacteria. The production of large concentrations of ammonia in the biodigestion process can raise pH and inhibit other desirable digestion processes, such as contemporaneous methanogenesis. Thus, co-digestion with high protein substrates that result in reduced production of inhibitory chemicals (e.g., hydrogen sulfide) can improve ammonia production. Such co-digestion feedstocks include blood meal, blood, soy meal, soy derived proteins, meat meal (slaughter house waste), feather meal, fish and fish by-products, whey, milk, dairy by-products, alfalfa, corn, and sweet clover. Such proteinaceous co-substrates provide nutrients missing from biodigestion of low-protein materials and help to prevent inhibiting substances from affecting methanogenesis. Additional nutrient supplements that supply sodium, calcium, magnesium, and trace amounts of nickel, cobalt, molybdenum, and/or selenium can aid in counteracting the effects of increased ammonia production by the anaerobic digestion. In some embodiments, bacterial strains that are able to thrive and produce ammonia at higher pH levels may be selected for use in the biodigestor (e.g., *Methanolobus* strains such as *Methanolobus bombayensis*, *Methanolobus taylorii*, and *Methanohalophilus zhilinaeae*) to allow the pH of the digester to be higher without impairing ammonia production.

In some embodiments, the temperature of the biodigestor 1001 may be maintained in a range of about 30° C. and about 60° C. (e.g., between about 40° C. and about 50° C.). The temperature of the digestor may be maintained by a combination of the heat generated by the anaerobic metabolism of the anaerobic bacteria in the digestor 1001 and one or more heating mechanisms 1007 (e.g., a heat exchanger) through which the digestate may be passed and heated and then returned to the digestor 1001 to maintain a target temperature in the digestor 1001. The system may include a boiler 1008 that provides steam for a heat exchanger 1007. In some examples, the boiler 1008 may be fueled by methane gas that is generated in the digestor 1001 and then extracted by a methane/$CO_2$ separation system 1010.

The pH of the biodigestor 1001 may be maintained in a pH range of about 6.5 to about 9 (e.g., in a range of about 6.8 to about 7.5, about 7 to about 9.5 or any value therein). In some examples, the pH of the digestor 1001 may be maintained at the pre-determined range by the combination of the degassing and removal of $CO_2$ from the digestate liquid and the addition of a basic agent into digestor as needed. For example, the digestor 1001 may include one or more pH meters that are in communication with an electronic controller (not shown) that is operable to control a valve and pump for releasing a basic agent of predetermined concentration and known basicity from a storage container 1051 housing the basic agent. The basic agent may be NaOH, $Ca(OH)_2$, KOH, or other basic agent.

The ammonia-rich liquid effluent generated in the digestor 1001 may subsequently be used in the ammonia extraction process performed in a series of desorption and absorption stages in which the physical conditions of the effluent (e.g., temperature and pH) are varied to facilitate removal and reabsorption of ammonia in aqueous solution. Digestate liquid in the digestor may decarbonized (dissolved carbon dioxide and carbonic acid may be removed), removing a significant amount of $CO_2$. The removal of carbon dioxide from the digestate fluid raises the pH of the digestate which drives the equilibrium of ammonium carbonate towards dissociation. Methane may also be produced in the digestor by the anaerobic bacteria. The methane and $CO_2$ gas that evolves in the digestor 1001 and may be collected via ducting and transferred to the methane/$CO_2$ separation system 1010. The separated methane may be utilized as a fuel for the boiler 1008 for providing heated water or other fluid to the heat exchanger 1007 and/or in other heating elements in the system 1000 for heating fluids at various stages of the ammonia recovery process. The methane may additionally or alternatively used as a fuel for an electric generator 1011. The recovered $CO_2$ may be vented out of the system 1000 and/or routed to mix with a recovered ammonia vapor in one or more of the desorption and absorption stages.

The decarbonized digestate fluid from the digestor 1001 may be collected and passed through a heating mechanism, such as the heat exchanger 1007, to further heat the digestate fluid and drive additional carbon dioxide out of solution. The temperature of the digestate fluid may be raised to a temperature of about 50° C. to about 100° C., and preferably greater than 60° C. The heated digestate fluid may subsequently passed from the heat exchanger 1007 to a sequence of mixing chambers in which the digestate fluid may manipulated to extract an ammonia solution.

FIG. 2 provides a view of an exemplary sequence of mixing units 1020, 1030, and 1040 through which substrates of the system may be transferred sequentially. Each of the mixing chambers may include an air nozzle or Venturi injector tube utilized to mix the fluid passed from one chamber to another with air or another gas. The temperature and pH conditions of each mixing chamber may be different in order to perform different absorption and desorption steps, which include decarbonization of the digestate (e.g., in mixing unit 1020), desorption of ammonia from the decarbonized digestate (e.g., in mixing unit 1030), and ammonia reabsorption in an aqueous solution (e.g., in mixing unit 1040).

The first mixing unit 1020 may include a nozzle or a Venturi-style injector tube 1021, and a collection chamber 1022. The digestate is mixed with air by the Venturi tube 1021 as the digestate passes therethrough. The Venturi tube 1021 includes a conduit 1021a through which the digestate is passed to a low-pressure choke point where an injection duct 1021b is located. Air (e.g., ambient air, air drawn from a pressurized tank, etc.) is injected through the injection duct 1021b to mix with the heated digestate. The air is mixed thoroughly with the digestate in the turbulent flow of the Venturi tube 1021, which provides a high degree of surface area interface between the digestate fluid and the injected air. This results in an enhanced degassing of $CO_2$ from the digestate. Once the digestate/air mixture passes into the mixing chamber 1022 in which the digestate/air mixture settles, and the $CO_2$-rich air bubbles out of the digestate fluid. The digestate that pools in the mixing chamber 1022 may also be heated to a temperature in a range of about 85° C. to about 100° C. The resulting decarbonized digestate may have a pH of about 6.8 to about 9 (e.g., about 7.5 to about 8.5, or any value in such range). The $CO_2$-rich air may be removed from the chamber for use in a later stage of the ammonia recovery process. The removal of the $CO_2$-rich air may be aided by a pump, a partial vacuum, or may be allowed to flow naturally from the chamber. The decarbonization process of the present invention may remove up to about 90% of the $CO_2$ from the effluent, thereby pushing the chemical equilibrium of ammonium bicarbonate and ammonia significantly toward free ammonia and increase the pH of the digestate fluid, thereby facilitating an extraction of a greater quantity of ammonia from the effluent.

Carbon dioxide and digestate may be collected from the first mixing unit 1020 and transferred to further mixing chambers in a sequential absorption and desorption stages. The carbon dioxide and/or digestate may also be transferred to other structures and uses in the system 1000. The decarbonized digestate fluid from the first mixing unit 1022 may be transferred from the mixing chamber 1022 to the input conduit 1031a of the Venturi tube 1031, and the decarbonized digestate is passed to a low-pressure choke point where an injection duct 1031b is located. Air (e.g., ambient air, air drawn from a pressurized tank, etc.) is injected through the injection duct 1031b to mix with the heated decarbonized digestate. The air is mixed thoroughly with the digestate in the turbulent flow of the Venturi tube 1031, resulting in a large volume of air mixing into the decarbonized digestate which enhances volatilization of $NH_3$ from the decarbonized digestate. The increased pH of the decarbonized digestate fluid pushes ammonium equilibrium toward dissociation of ammonium into aqueous ammonia and hydrogen ions, making more ammonia available in the digestate fluid and facilitating volatilization of ammonia from the digestate fluid. The decarbonized digestate at a high temperature and an increased pH allows a large majority of the ammonium in the digestate fluid being dissociated into ammonia and hydrogen ions, allowing a proportion of the ammonia in solution that is in the uncharged (non-ionized) ammonia state of about 0.6 or greater. The solubility of $NH_3$ in an aqueous solution is low, and thus most of the $NH_3$ volatilizes from the digestate fluid, and can be collected.

In some examples, the decarbonized digestate fluid may be routed to a heat exchanger or other heating apparatus 1027 to further raise the temperature of the decarbonized digestate fluid to a temperature in a range of about 70° C. to about 90° C. (e.g., about 75° C. to about 80° C., or any value or range of values therein) prior to passing through the Venturi tube 1031. The proportion of ammonia that is in the $NH_3$ form in a aqueous solution (1) at a temperature in a range of 70° C. to about 80° C. and (2) a pH of about 8 to about 10 (e.g., in a range of about 8.5 to about 9.5) is in a range of about 0.6 to about 0.95. In some embodiments, the air drawn into the mixing chamber 1032 may be warmed using a heat exchanger, heating coil or other heating mechanism to raise the temperature of the incoming air to a temperature in a range, e.g., of 70° C. to about 90° C. to aid in raising the temperature of the decarbonized digestate. An ammonia-rich air mixture is collected from the chamber through a collection conduit 1033 to transfer the $NH_3$ rich mixture to a later stage of the ammonia recovery process. The removal of the ammonia-rich vapor may be aided by a pump, applied partial vacuum, or may be allowed to flow naturally from the chamber.

In some embodiments, one or more basic chemical agents may be used to raise the pH of the digestate fluid pooled in the second mixing chamber 1032. In some examples, the basic agent may be NaOH, $Ca(OH)_2$, KOH, or other basic agent, which may be added in sufficient amounts to raise the pH of the pooled digestate to a pH in the range of about 9 to about 11 (e.g., about pH 9.5 to about pH 10.5) to further shift the ammonia equilibrium toward de-ionized ammonia. The basic agent may be supplied from the storage container 1051 housing the basic agent.

In some embodiments, some or all of the digestate fluid remaining in the second mixing chamber 1032 may be removed from the chamber and routed either back to the digester 1001 or delivered into a filtering apparatus 1052 (e.g., a filter press) for purification. The filtering apparatus may be any of various known filtering apparatus. Once the recovered fluid is filtered, yielding a water filtrate, the water may be conditioned to a target temperature and routed to one or more subsequent uses. The recovered digestate fluid may be conditioned in a heating system (e.g., a heat exchanger electrical heating system, etc.) to a temperature in a range of about 35° C. to about 45° C. and routed in a tank 1053 for storage. The fluid may be added back to the digester to be mixed with the biodigestion medium as needed. After filtering, the fluid may also or alternatively be conditioned to a temperature of about 70° C. to about 90° C. (e.g., about 75° C. to about 80° C., or any value or range of values therein) using a heat exchanger or other heating mechanism and may be added back to the fluid of the second mixing chamber 1032 as needed. The filtered fluid may also be conditioned with a pH agent (e.g., sodium hydroxide or hydrated lime, etc.) to raise the pH before it is added back to the second tank. Keeping the digestate pooled in the second mixing tank 1032 allows for a building $NH_3$ concentration in the fluid in the second mixing tank 1032 to increase the amount of $NH_3$ that volatilized from the fluid in the second mixing tank 1032.

The significant amounts of $NH_3$ that volatilize from the digestate fluid in the second mixing chamber 1032 and may be collected via an outlet 1034 that leads to a third air nozzle or Venturi injector 1041 and third mixing chamber 1042. The $NH_3$-rich air collected from the second mixing chamber 1032 may be passed through the injector duct 1041b of the third Venturi injector 1041 and mixed at the throat of the Venturi tube with the cooled aqueous $NH_3$ solution (less than about 20° C.), which has a pH of less than about 8.5 that is passed through the input passage 1041a of the Venturi mixer

1041. Thus, the relatively warm $NH_3$ vapor from the second mixing chamber 1032 is mixed with a cooled $NH_3$ solution to reduce the temperature to allow the gaseous $NH_3$ vapor to be reabsorbed into the cooled $NH_3$ solution. The lower pH of the cooled $NH_3$ solution also allows for reabsorption of the $NH_3$ vapor. In some embodiments, $CO_2$ gas captured evolved and collected from the digestate fluid in the first mixing chamber 1022 may be routed from outlet 1024 to the injector duct 1041b of the third mixing unit 1040 and mixed with the $NH_3$-rich air collected from the second mixing chamber 1032. The added $CO_2$ gas may be used as the means by which the pH of the third mixing chamber 1042 is reduced in order to increase the amount of dissolved $NH_4^+$ in the fluid collected in the third mixing chamber 1042. In some embodiments, the $CO_2$ gas may be cooled in a heat exchanger or other mechanism prior to it being delivered to the injector duct 1041b of the third Venturi mixer 1041. In other embodiments, the cooled fluid may be a pH treated solution comprising a weak acid and/or buffering agents to maintain the pH below about 8.5. A substantial amount of the $NH_3$ in the air mixture is able to be dissolved into the cooled, lower pH aqueous solution in the third mixing chamber 1032 because ammonia solubility in aqueous solutions increases as temperature and pH drop. The proportion of ammonia that is in the $NH_4^+$ form in an aqueous solution (1) at a temperature in a range of 20° C. or less and (2) a pH of less than about 8.5 to greater or equal to about 0.8. Thus, the solubility of $NH_3$ in aqueous solution is also high, and thus a significant proportion of the $NH_3$ in the $NH_3$-rich air dissolves into the ammonia solution.

In some embodiments, the cooled fluid passed through the Venturi mixer may be fluid taken from the third mixing chamber 1042 and either routed to the intake 1041a of the Venturi mixer 1041 or routed to a cooling tank 1053 (e.g., including a heat exchanger, refrigeration unit, or other cooling mechanism) to lower the temperature to a temperature in a range of about 10° C. to about 20° C. before being passed to the intake 1041a to mix with the $NH_3$-rich air from the second mixing chamber 1032. The fluid from the third mixing chamber 1042 may be delivered to the intake 1041a at a pre-determined rate.

The ammonia-rich aqueous solution collected in the third mixing chamber 1042 may be transported through outlet 1043 incrementally to a collection tank 1054 for the clean aqueous ammonia product. The ammonia-rich aqueous solution may be used in a number of applications including making organic nitrogen fertilizers. Because the ammonia is organically derived from biowastes and natural sources, the concentration of the stable $^{15}N$ isotope in the resulting ammonia composition is much higher than in ammonia products that are made from chemical syntheses and concentration techniques. The $^{15}N$ isotope is present in the environment and in ammonia products produced by chemical reactions in an amount of about 0.3% per mole of naturally occurring nitrogen. The amount of $^{15}N$ isotope in the ammonia and related species produced by the process of the present invention is in the range of about 1% to about 20% per mole of nitrogen (e.g., in a range of about 5% to about 15%). The high concentration of $^{15}N$ isotope reflects the process of concentrating ammonia from natural biowastes and nutrient stocks through organic processes.

The ammonia produced by this process is an organic ammonium hydroxide solution that is usable in organic farming. The ammonia is produced at a concentration in a range of about 3-30% w/w ammonia solution (e.g., about 10% to about 25% w/w ammonia). The organic ammonia solution may be used to create fertilizer compositions that are compliant with the Organic Foods Production Act of 1990, USDA Organic Regulations, (generally referred to as the National Organic Program or NOP) and other agency standards for use in organic farming and can be used in organic farming operations.

In some embodiments, and without limitation, a fertilizer composition may include a liquid composition that includes about 3% to about 30% ammonia w/w (e.g., 10% w/w to about 25% w/w, or any value or range of values therein), and/or one or more additional ingredients. The fertilizers may further include organic acids that may serve to balance the pH effects of the concentrated ammonia in the fertilizer. The pH may be maintained in a range around neutral pH, such as between about pH 6 and pH 8 (e.g., from about pH 6.5 to about pH 7.5). To balance the pH of the liquid fertilizer, the liquid fertilizer may include one or more organic acids.

The resulting high concentration ammonia composition may be further processed into fertilizer products. In some embodiments, the fluid product captured from the third mixing chamber may be utilized as a fertilizer composition. Such fertilizer composition may be an aqueous solution comprising ammonia and ammonium species (e.g., $NH_4^+$, ammonium hydroxide, and ammonium carbonate) in a concentration of about 3% to about 30% w/w (e.g., 10% w/w to about 25% w/w, or any value or range of values therein), and carbonic acid in various soluble forms in an amount of about 5% to about 15% w/w. In some embodiments, the ammonia-rich aqueous solution may be mixed with other plant and soil nutrient compounds that are compatible with organic farming to create a nitrogen-rich organic fertilizer composition.

The high concentration ammonia composition may be mixed with alternative acids, including organic acids. In some embodiments, the fertilizer composition may be an aqueous solution comprising ammonia and ammonium species (e.g., $NH_4^+$, ammonium hydroxide, and ammonium carbonate) in a concentration of about 3% to about 30% w/w (e.g., 10% w/w to about 25% w/w, or any value or range of values therein), and citric acid in various soluble forms in an amount of about 5% to about 15% w/w, to yield a combination of these species with ammonium citrate (see FIG. 1). A reservoir of citric acid may be included in the system 1000, and at least a portion of the high concentration ammonia composition produced by the system may be mixed with the citric acid from the citric acid reservoir to produce a separately collected and stored product comprising organic ammonia, ammonium species (including ammonium citrate), and citric acid.

In other embodiments, the organic fertilizers may include ammonia in various ionic forms in a concentration of about 3% to about 30% w/w (e.g., 10% w/w to about 25% w/w, or any value or range of values therein) and one or more weak organic acids or salts thereof (e.g., polyprotic organic acids or salts thereof), such as citric acid, malic acid, fumaric acid, salts of such organic acids, and combinations thereof. Other simpler organic acids, such as acetic acid salts of such organic acids may be used as well. The organic acids must be from organically-compliant sources (e.g., NOP compliant). Citric acid may be preferred due to its tri-protic chemistry and superior buffering capabilities. The organic acid(s) may be present in a concentration in the liquid fertilizer in a range of about 5% to about 50% w/w, depending on the concentration of ammonia in the liquid fertilizer. For example, the concentration of citric acid in the liquid fertilizer by weight may be about twice the amount of ammonia present in the solution by weight. Simpler monoprotic acids may be present in higher concentrations, due to their lower buffering capacity.

The organic fertilizers of the present invention may also include humic acids which help with nitrogen fixation in the organic fertilizers. Liquid ammonia fertilizers suffer from nitrogen loss through evaporation or other pathways of loss. Planting soils are typically acidic to optimize conditions for the growth of plants, which exhibit optimal germination and growth in a pH range of about pH 5.0 to about pH 7.0. The acidic pH of the soil can increase ammonia volatilization. This particularly significant where the fertilizer composition has a relatively high nitrogen concentration (e.g., greater than 10% w/w), since the higher concentration results in a higher rate of volatilization. Humic acids are able to retain $NH_4$ as well as aid in $NH_3$ ammonia volatilization reduction. Humic acids have high cation exchange capacity (CEC) that allows it to retain soil cations and can significantly reduce $NH_3$ volatilization upon addition to an acidic soil (e.g., through the addition of peat). The addition of humic acids to the organic $NH_3$ fertilizer of the present invention significantly reduces $NH_3$ volatilization and lead to effective accumulation of $NH_4$ in the planting soil, despite having an acidic pH (e.g., about pH 5.5 to about 7.0). The humic acids may provide the additional benefit of providing short carbon-chain molecules.

Humic acids may be included in the organic fertilizer composition of the present invention in a concentration in a range of about 3% w/w to about 8% w/w. The amount of humic acids included in the organic fertilizer may vary with the concentration of ammonia provided therein. For example, in compositions comprising about 10% to about 15% $NH_3$ w/w, the fertilizer composition may include about 3% to about 4% w/w of humic acids. In compositions comprising about 15% to about 25% organic $NH_3$ w/w, the fertilizer composition may include about 5% to about 8% w/w of humic acids.

The organic fertilizer composition of the present invention may also include additional components routinely used in the art, for example, humectants, adjuvants, antioxidants, stabilizers, plant macronutrients, plant micronutrients, and combinations thereof.

The organic fertilizer composition of the present invention may also include a solid fertilizer composition comprising about 3% to about 30% ammonia w/w (e.g., 10% w/w to about 25% w/w, or any value or range of values therein), and/or one or more additional ingredients. The fertilizers may further include organic acids that may serve to balance the pH effects of the concentrated ammonia in the fertilizer. The pH may be maintained in a range around neutral pH, such as between about pH 6 and pH 8 (e.g., from about pH 6.5 to about pH 7.5). The solid fertilizer composition may additionally include humectants, adjuvants, antioxidants, stabilizers, plant macronutrients, plant micronutrients, and combinations thereof. The fertilizer composition may include further nutrients, such as gypsum as a calcium sulfate source, and dolomitic lime as a calcium carbonate and magnesium carbonate source.

CONCLUSION/SUMMARY

The present invention provides organic ammonia fertilizer compositions and methods of making the same. It is to be understood that variations, modifications, and permutations of embodiments of the present invention, and uses thereof, may be made without departing from the scope of the invention. It is also to be understood that the present invention is not limited by the specific embodiments, descriptions, or illustrations or combinations of either components or steps disclosed herein. The embodiments were chosen and described in order to best explain the principles of the invention and its practical application, to thereby enable others skilled in the art to best utilize the invention and various embodiments with various modifications as are suited to the particular use contemplated. Although reference has been made to the accompanying figures, it is to be appreciated that these figures are exemplary and are not meant to limit the scope of the invention. It is intended that the scope of the invention be defined by the claims appended hereto and their equivalents.

What is claimed is:

1. A method of producing organic ammonia, comprising:
    a. heating a nitrogen-containing organic substrate in an anaerobic digester device to drive a biological anaerobic digestion of the substrate to yield a digestate;
    b. collecting an effluent of the digestate;
    c. mixing the effluent with air, and heating said effluent in a first chamber separate from said digester to evolve $CO_2$-laden gas from the effluent and collecting said $CO_2$-laden gas from said first chamber to yield a decarbonized effluent in the first chamber;
    d. aerating said decarbonized effluent with air and heating the decarbonized effluent-air mixture to evolve $NH_3$ from said decarbonized effluent in a second chamber and removing $NH_3$ vapor; and
    e. cooling the $NH_3$ vapor to yield an aqueous $NH_3$ product derived from said nitrogen-containing organic substrate without chemical reactions.

2. The method of claim 1, wherein mixing the effluent with air comprises injecting air into the effluent by passing the effluent through a first Venturi injector tube and injecting air into the effluent through an injection port.

3. The method of claim 2, wherein said aerating the decarbonized effluent to evolve said $NH_3$ from the decarbonized effluent includes passing the decarbonized effluent through a second Venturi injector tube and injecting air into the decarbonized effluent through a second injection port.

4. The method of claim 1, further comprising injecting said $NH_3$ vapor into a cooled aqueous $NH_3$ solution to resorb $NH_3$ from the $NH_3$ vapor during said step of cooling the $NH_3$ vapor, wherein injecting said $NH_3$ vapor into a cooled aqueous $NH_3$ solution includes passing the cooled aqueous $NH_3$ solution through a third Venturi injector tube and injecting the $NH_3$ vapor into the cooled aqueous $NH_3$ solution through a third injection port.

5. The method of claim 1, further comprising transferring the decarbonized effluent to a filtering apparatus and filtering the decarbonized effluent to yield water, and supplying said water to a collection chamber.

6. A method of producing organic ammonia, comprising:
    a. heating a nitrogen-containing organic substrate in a digestion chamber to yield a nitrogen-rich digestate;
    b. collecting an effluent of the digestate;
    c. heating said effluent to evolve $CO_2$-laden gas from the effluent in a first chamber to lower a pH of said effluent and to produce a decarbonized effluent;
    d. passing the decarbonized effluent through Venturi injector tube and injecting air into the decarbonized effluent to cause degassing of $NH_3$ vapor within a second chamber; and
    e. collecting and cooling the $NH_3$ vapor in a third chamber to yield an aqueous $NH_3$ solution.

7. The method of claim 6, wherein said step of heating said effluent drives the chemical equilibrium of ammonium bicarbonate toward the production of $NH_3$ and $CO_2$.

8. The method of claim 6, further comprising injecting air into the effluent during the step of heating said effluent to produce said decarbonized effluent, wherein injecting air into the effluent includes passing the effluent through a second Venturi injector tube and injecting air into the effluent through the Venturi injection port.

9. The method of claim 6, further comprising injecting said $NH_3$ vapor into said aqueous $NH_3$ solution to resorb $NH_3$ from the $NH_3$ vapor, wherein injecting said $NH_3$ vapor into said aqueous $NH_3$ solution includes passing the aqueous $NH_3$ solution through a third Venturi injector tube and injecting the $NH_3$ vapor into the aqueous $NH_3$ solution through the Venturi injection port of the third Venturi injector tube.

10. The method of claim 6, further comprising adding a basic chemical agent to the decarbonized effluent before or during the step of extracting $NH_3$ from said decarbonized effluent.

11. The method of claim 6, further comprising transferring the decarbonized effluent to a filtering apparatus and filtering the decarbonized effluent to yield water, and supplying said water to a collection chamber.

12. The method of claim 6, further comprising injecting $CO_2$ into said aqueous $NH_3$ solution to lower the pH of the aqueous $NH_3$ solution to aid in resorbing $NH_3$ from the $NH_3$ vapor, wherein injecting said $CO_2$ into said aqueous $NH_3$ solution includes passing the aqueous $NH_3$ solution through a third Venturi injector tube and injecting the $CO_2$ into the aqueous $NH_3$ solution through the Venturi injection port of the third Venturi injector tube.

13. A method of producing organic ammonia, comprising:
  a. collecting a nitrogen-containing effluent from an anaerobic digestion process;
  b. mixing the effluent with air, and heating said effluent in a first chamber separate from an anaerobic digester to evolve $CO_2$-laden gas from the effluent to yield a decarbonized effluent in the first chamber;
  c. aerating said decarbonized effluent with air and heating the decarbonized effluent-air mixture to evolve $NH_3$ from said decarbonized effluent in a second chamber and removing $NH_3$ vapor; and
  d. cooling the $NH_3$ vapor to yield an aqueous $NH_3$ product derived from said effluent.

14. The method of claim 13, wherein mixing the effluent with air comprises injecting air into the effluent by passing the effluent through a first Venturi injector tube and injecting air into the effluent through an injection port.

15. The method of claim 14, wherein said aerating the decarbonized effluent to evolve said $NH_3$ from the decarbonized effluent includes passing the decarbonized effluent through a second Venturi injector tube and injecting air into the decarbonized effluent through a second injection port.

16. The method of claim 13, further comprising injecting said $NH_3$ vapor into a cooled aqueous $NH_3$ solution to resorb $NH_3$ from the $NH_3$ vapor during said step of cooling the $NH_3$ vapor, wherein injecting said $NH_3$ vapor into a cooled aqueous $NH_3$ solution includes passing the cooled aqueous $NH_3$ solution through a third Venturi injector tube and injecting the $NH_3$ vapor into the cooled aqueous $NH_3$ solution through a third injection port.

17. The method of claim 16, further comprising concentrating said aqueous $NH_3$ solution to a concentration of $NH_3$ and other ammoniacal species in a range of about 3% to about 30% by weight.

18. The method of claim 13, wherein said heating said effluent drives the chemical equilibrium of ammonium bicarbonate toward the production of $NH_3$ and $CO_2$.

19. The method of claim 13, further comprising transferring the decarbonized effluent to a filtering apparatus and filtering the decarbonized effluent to yield water, and supplying said water to a collection chamber.

* * * * *